United States Patent
Gschneidner

(10) Patent No.: US 8,148,578 B2
(45) Date of Patent: Apr. 3, 2012

(54) FAST ACTING NARATRIPTAN COMPOSITION

(75) Inventor: David Gschneidner, Cedar Knolls, NJ (US)

(73) Assignee: Emisphere Technologies Inc., Cedar Knolls, NJ (US)

( * ) Notice: Subject to any disclaimer, the term of this patent is extended or adjusted under 35 U.S.C. 154(b) by 0 days.

(21) Appl. No.: 13/208,644

(22) Filed: Aug. 12, 2011

(65) Prior Publication Data

US 2011/0301244 A1    Dec. 8, 2011

Related U.S. Application Data

(63) Continuation of application No. 12/415,954, filed on Mar. 31, 2009, now Pat. No. 8,076,333.

(60) Provisional application No. 61/040,998, filed on Mar. 31, 2008.

(51) Int. Cl.
*C07C 211/00* (2006.01)
(52) U.S. Cl. .......... 564/305; 564/336; 564/337
(58) Field of Classification Search .......... 564/305, 564/336, 337
See application file for complete search history.

(56) References Cited

U.S. PATENT DOCUMENTS

2010/0151009 A1    6/2010    Levchik

*Primary Examiner* — Jennifer M Kim
(74) *Attorney, Agent, or Firm* — Blank Rome LLP

(57) ABSTRACT

The present invention relates to pharmaceutical compositions containing Naratriptan, a compound selected from the group consisting of 2-HPOD, 2-HPHM, 4-PPED, 4-BPED and 2-PPED, and optionally, a pharmaceutically acceptable excipient.

11 Claims, 1 Drawing Sheet

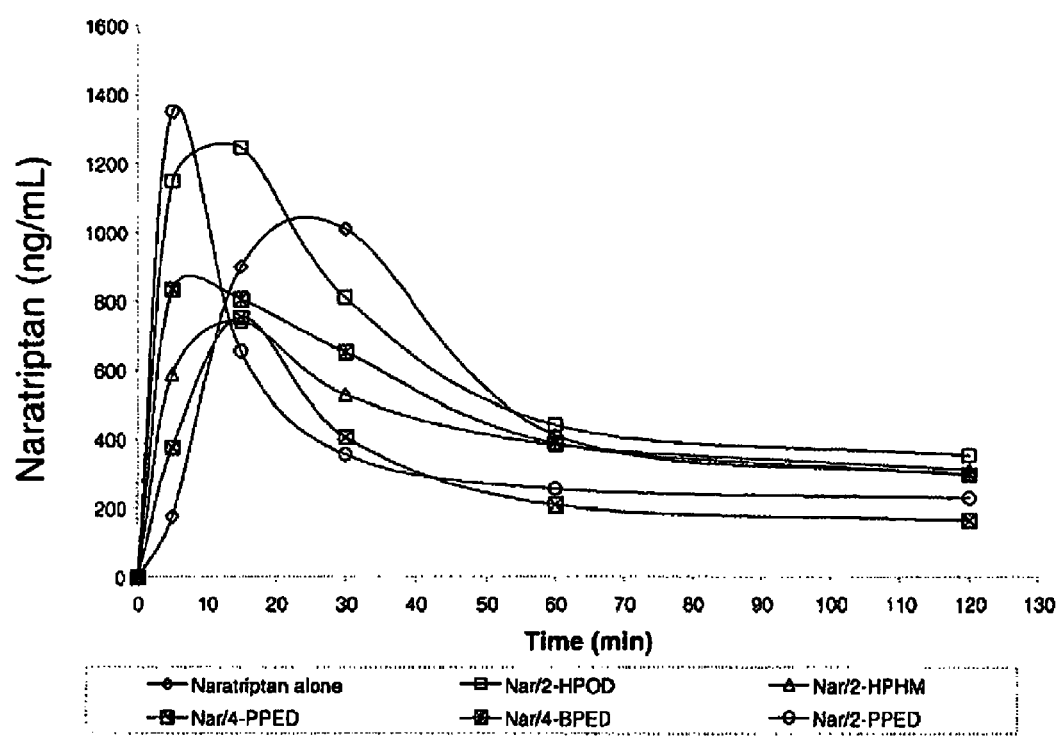

FAST ACTING NARATRIPTAN COMPOSITION

This application is a continuation of U.S. patent application Ser. No. 12/415,954, filed Mar. 31, 2009, which claims the benefit of U.S. Provisional Application No. 61/040,998, filed Mar. 31, 2008, each of which is incorporated herein by reference in its entirety.

FIELD OF THE INVENTION

The present invention relates to pharmaceutical compositions containing naratriptan and a compound selected from the group consisting of 2-HPOD, 2-HPHM, 4-PPED, 4-BPED and 2-PPED and methods of using such compositions for treating migraine headaches.

BACKGROUND OF THE INVENTION

Migraine typically begins with mild to moderate pain that increases in severity over several hours to reach peak severity. The painful phase of the migraine attack persists for 6 to 12 hours in most migraine patients. For those with migraines, the two most important features of migraine medications are providing quick relief and effectively decreasing pain. Migraine patients are dissatisfied with the amount of time to obtain pain relief after taking migraine medication. One group of very effective migraine pain relievers are triptans. The onset of relief or action of the triptans is measured by the rapid time to peak blood concentration ($T_{max}$). Migraine patients reported relief of migraine related disability within 2 hours after dosing with a triptan. Migraine patients need rapid relief from their pain and desire a faster time to headache relief. (see Dawn A. Marcus, M.D., "Establishing a Standard of Speed for Assessing the Efficacy of the Serotonin$_{IB/ID}$ Agonists (Triptan)" *Arch Neurol/Volume* 58, June 2001 available on www.archneurol.com)

Naratriptan has been marketed under the trade name Amerge® by Glaxo Wellcome in the U.S. in tablets (2.5 mg) for oral administration. Naratriptan is a member of the drug class known as serotonin (5HT) agonists and has been used as a pharmaceutical agent to successfully treats acute migraines. Naratriptan tablets are well absorbed, with about 70% oral bioavailability. Following administration of a 2.5 mg tablet orally, the peak concentrations are obtained in 2 to 3 hours. During a migraine attack, absorption was slower, with a $T_{max}$ of 3 to 4 hours.

Because migraine patients desire to return back to their daily task in life within a short time after taking migraine medication, there is a need to have rapid, complete relief of migraine pain within less than 2 hours after drug administration. So far, various efforts to improve the peak concentrations of Naratriptan have failed.

SUMMARY OF THE INVENTION

The present invention provides a pharmaceutical composition for treating migraines in a subject with a shortened time period for the onset of maximum peak concentration, comprising of: (a) naratriptan or its salt thereof, (b) at least one compound selected from the group consisting of 2-HPOD, 2-HPHM, 4-PPED, 4-BPED and 2-PPED and (c) optionally, a pharmaceutically acceptable excipient.

The present invention also provides a tablet for rapid onset of therapeutic effects in treating migraines comprising of a (1) about 0.1 mg to about 100 mg of naratriptan, and (2) from about 10 mg to about 500 mg of at least one of 2-HPOD, 2-HPHM, 4-PPED, 4-BPED and 2-PPED.

The present invention further provides a method of treating migraine headaches, comprising the step of administering the pharmaceutical composition which contains (a) naratriptan or its salt thereof, (b) at least one compound selected from the group consisting of 2-HPOD, 2-HPHM, 4-PPED, 4-BPED and 2-PPED and (c) optionally, a pharmaceutically acceptable excipient, in a subject in need of such a treatment, wherein said pharmaceutical composition, upon oral administration, takes at least 20% less time to reach $T_{max}$ in comparison to administering naratriptan alone.

The contents of the patents and publication cited herein and the contents of documents cited in these patents and publications are hereby incorporated herein by reference to the extent permitted.

BRIEF DESCRIPTION OF THE DRAWINGS

FIG. 1 is a graph showing the mean plasma concentrations of naratriptan in rats following a single oral administration of naratriptan (10 mg/kg) alone or in combination with one of 2-HPOD, 2-HPHM, 4-PPED, 4-BPED and 2-PPED (200 mg/kg).

DETAILED DESCRIPTION OF THE INVENTION

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to pharmaceutical compositions can mean a range of up to 10%, preferably up to 5%.

The phrase "pharmaceutically acceptable" refers to compounds or compositions that are physiologically tolerable and do not typically produce an allergic or similar untoward reaction, such as gastric upset, dizziness and the like, when administered to a mammal.

As used herein, the term "treat" or "treating" includes one or more of the following: (a) arresting, delaying the onset (i.e., the period prior to clinical manifestation of a disorder) and/or reducing the risk of developing or worsening a disorder; (b) relieving or alleviating at least one symptom of a disorder in a mammal, including for example, hypercalcemia; or (c) relieving or alleviating the intensity and/or duration of a manifestation of a disorder experienced by a mammal including, but not limited to, those which are in response to a given stimulus (e.g., pressure, tissue injury or cold temperature). The term "treat" also includes prophylactically preventing, curing, healing, alleviating, relieving, altering, remedying, ameliorating, improving, or affecting a condition (e.g., a disease), the symptoms of the condition, or the predisposition toward the condition.

The term "bioavailability" refers to the rate and extent to which the active ingredient or active moiety is absorbed from a drug product and becomes systematically available.

The term "2-HPOD" refers to 8-(2-hydroxyphenoxy)octyldiethanolamine and pharmaceutically acceptable salts. 8-(2-hydroxyphenoxy)octyldiethanolamine has the following chemical structure:

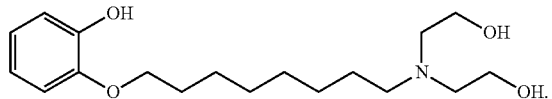

The term "2-HPHM" refers to 6-(2-hydroxyphenoxy)hexylmorpholine and its pharmaceutically acceptable salts. 6-(2-hydroxyphenoxy)hexylmorpholine has the following chemical structure:

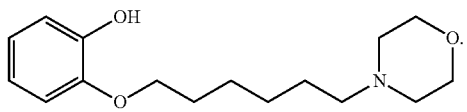

The term "4-PPED" refers to 2-(4-phenoxyphenyl)ethyldiethanolamine its pharmaceutically acceptable salts. 2-(4-phenoxyphenyl)ethyldiethanolamine has the following chemical structure:

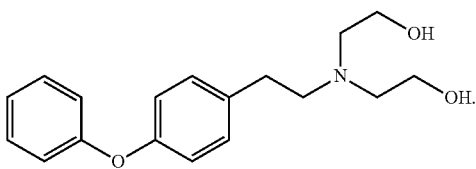

The term "4-BPED" refers to 2-(biphen-4-yl)ethyldiethanolamine and its pharmaceutically acceptable salts. 2-(biphen-4-yl)ethyldiethanolamine has the following chemical structure:

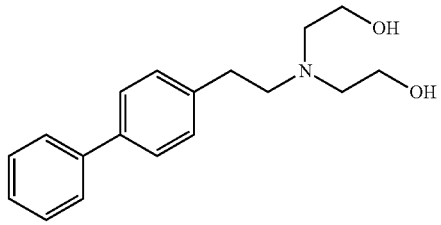

The term "2-PPED" refers to 2-(2-phenoxyphenyl)ethyldiethanolamine and its pharmaceutically acceptable salts. 2-(2-phenoxyphenyl)ethyldiethanolamine has the following chemical structure:

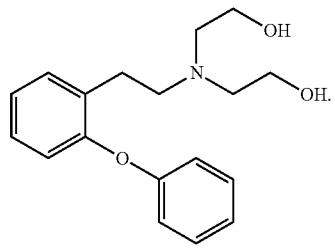

The term "$AUC_{0\text{-}last}$" refers to area under the curve to the last quantifiable time point. The term "$C_{max}$" refers to peak plasma concentration. $C_{max}$ is the maximum absorption of the Naratriptan into the mammal's blood stream. The term "$T_{max}$" refers to mean time-to-peak concentrations. A shorter $T_{max}$ correlates with a more rapid onset of action and quicker pain relief in mammals.

In one embodiment of the present invention, a naratriptan salt is used in the pharmaceutical composition. Such salt includes hydrochloride, hydrobromide, mesylate, acetate, trifluoroacetate, propionate, fumarate, tartrate, citrate, phosphate, succinate, bisulfate, and besylate salts.

In another embodiment of the present invention, the pharmaceutical composition contains naratriptan and one of 2-HPOD, 2-HPHM, 4-PPED, 4-BPED and 2-PPED in a weight ratio from about 1:100 to about 1:5, preferably from about 1:75 to about 1:4, more preferably from about 1:50 to about 1:2 and the most preferably from about 1:50 to about 1:1.

In another embodiment of the present invention, the method of treating migraine headaches achieves $T_{max}$ in a subject, upon oral administration of the pharmaceutical composition, in at least 20% less time in comparison to administering naratriptan alone, preferably in at least 40% less time, more preferably in at least 50% less time, more preferably in at least 60% less time, in at least 70% less time, more preferably in at least 75% less time and the most preferably in at least 80% less time.

In the present invention, the delivery system is the pharmaceutical formulations which may be in the form of a liquid or solid. Liquid formulations may be water-based. The absorption enhancer was dissolved in deionized water. 10 N NaOH solution was used to help dissolving acid form carriers. HCl was added to lower pH of the absorption enhancer stock solution if the pH was higher than 7.4. Naratriptan powder was added to the absorption enhancer solution 5 minutes before dosing. The final concentration of drug was 10 mg/ml, and the final concentration of carrier was 200 mg/ml for the study.

The following examples are given as specific illustrations of the invention. It should be understood, however, that the invention is not limited to the specific details set forth in the examples. All parts and percentages in the examples, as well as in the remainder of the specification, are by weight unless otherwise specified.

Example 1

The study was conducted in fasted adult male Sprague-Dawley rats (n=5 for each group as seen in FIG. 1). Naratriptan is also designated Nar. Naratriptan was administered alone to rates orally as a control. For oral dosing, single solutions were administrated at time 0, in the following manner: (a) each absorption enhancer carrier (200 mg/kg) in combination with Nar (10 mg/kg) was administered orally to rats; and (b) Nar (10 mg/kg) alone was administered orally to rats. Blood samples were collected by retro-orbital bleed under $CO_2$ anesthesia pre-dosing (0 minute), and 5, 15, 30, 40, 50, 60, 120 and 240 minutes after dosing. In the control study, where Naratriptan (10 mg/kg) alone was administered to rats, mean peak concentrations were achieved at 27 minutes post-dose. In the administration of Nar/2-HPOD combination, mean peak Naratriptan plasma concentration was observed at 13 minutes post-dose as opposed to 27 minutes as seen following Naratriptan alone. In the administration of Nar/2-HPHM combination, mean peak Naratriptan plasma concentration was observed at 12 minutes post-dose as opposed to 27 minutes as seen following Naratriptan alone. Both, the Nar/2-HPOD and Nar/2-HPHM combination took approximately ½ the time of Naratriptan alone. In the administration of Nar/4-PPED combination, mean peak Naratriptan plasma concentration was observed at 7.5 minutes post-dose as opposed to 27 minutes as seen following Naratriptan alone. Also the mean $C_{max}$ value of the Nar/4-PPED combination was approximately 2-fold higher compared to that obtained following Naratriptan alone. In the administration of Nar/4-BPED combination, mean peak Naratriptan plasma concentration was observed at 9 minutes post-dose as opposed to 27 minutes as seen following Naratriptan alone. In the administration of Nar/2-PPED combination, mean peak Naratriptan plasma concentration was observed at 28 minutes post-dose approximately the same time as seen following Naratriptan alone. However, the mean $C_{max}$ value of the Nar/2-PPED combination was significantly higher than as seen following Naratriptan alone. The testing data are shown in the following table.

| Group | AU Clast (min * ng/ml) | $C_{max}$ (ng/ml) | $T_{max}$ (min) |
| --- | --- | --- | --- |
| Naratriptan alone (10 mg/kg) | 62851 | 1052 | 27.0 |
| Naratriptan/2-HPOD (10 mg/kg) | 73568 | 1315 | 13.0 |
| Naratriptan/2-HPHM (10 mg/kg) | 26815 | 1095 | 12.0 |
| Naratriptan/4-PPED (10 mg/kg) | 52453 | 933 | 7.5 |
| Naratriptan/4-BPED (10 mg/kg) | 57587 | 940 | 9.0 |
| Naratriptan/2HPOD (10 mg/kg) | 43725 | 1357 | 28.0 |

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art, without departing from the spirit of the invention.

What is claimed is:

1. A compound selected from:

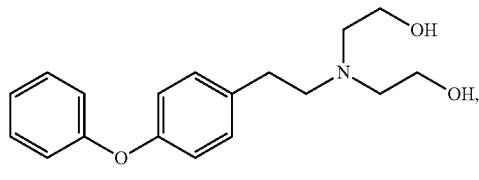

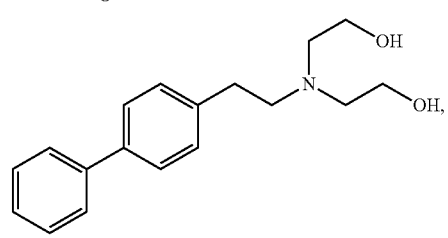

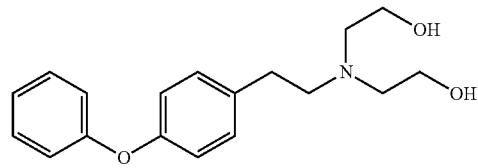

and pharmaceutically acceptable salts thereof.

2. The compound of claim 1, wherein the compound is

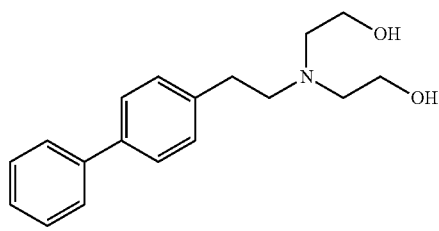

or a pharmaceutically acceptable salt thereof.

3. The compound of claim 1, wherein the compound is

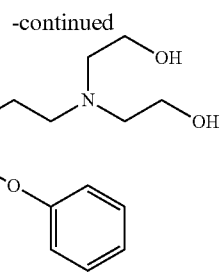

or a pharmaceutically acceptable salt thereof.

4. The compound of claim 1, wherein the compound is

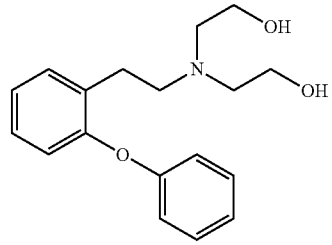

or a pharmaceutically acceptable salt thereof.

5. A pharmaceutical composition comprising a compound of claim 1 and a pharmaceutically acceptable excipient.

6. The pharmaceutical composition of claim 5, wherein the compound is

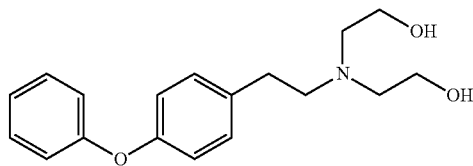

or a pharmaceutically acceptable salt thereof.

7. The pharmaceutical composition of claim 5, wherein the compound is

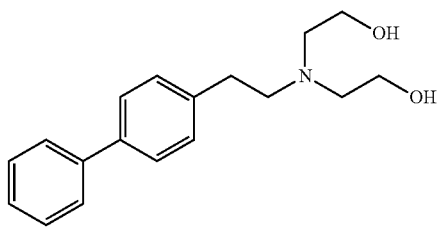

or a pharmaceutically acceptable salt thereof.

8. The pharmaceutical composition of claim 5, wherein the compound is

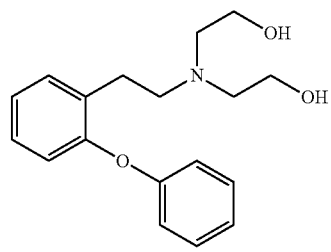

or a pharmaceutically acceptable salt thereof.

9. The pharmaceutical composition of claim 1, comprising from about 10 mg to about 500 mg of the compound.

10. The pharmaceutical composition of claim 1, wherein the pharmaceutical composition is in the form of a liquid or solid.

11. The pharmaceutical composition of claim 10, wherein the pharmaceutical composition is in the form of a solution.

* * * * *